(12) United States Patent
Kim et al.

(10) Patent No.: US 11,719,616 B2
(45) Date of Patent: Aug. 8, 2023

(54) OPTICAL ANALYSIS DEVICE AND OPTICAL ANALYSIS METHOD

(71) Applicant: Vieworks Co., Ltd., Anyang-si (KR)

(72) Inventors: Young Ho Kim, Seoul (KR); You Jung Kang, Anyang-si (KR)

(73) Assignee: Vieworks Co., Ltd., Anyang-si (KR)

( * ) Notice: Subject to any disclaimer, the term of this patent is extended or adjusted under 35 U.S.C. 154(b) by 371 days.

(21) Appl. No.: 17/090,612

(22) Filed: Nov. 5, 2020

(65) Prior Publication Data
US 2021/0130889 A1    May 6, 2021

(30) Foreign Application Priority Data

Nov. 6, 2019    (KR) .................... 10-2019-0140762

(51) Int. Cl.
*G01N 15/14* (2006.01)
*G01N 15/10* (2006.01)
*B01L 3/00* (2006.01)
*G01N 15/00* (2006.01)

(52) U.S. Cl.
CPC .... *G01N 15/1434* (2013.01); *B01L 3/502784* (2013.01); *G01N 15/1056* (2013.01); *B01L 3/502715* (2013.01); *G01N 2015/0065* (2013.01)

(58) Field of Classification Search
CPC ........ G16B 20/00; G16B 20/20; G16B 20/40; G16B 30/00; B01L 3/502715; B01L 3/502784; C12Q 1/6869; G01N 15/1056; G01N 15/1434; G01N 15/1456; G01N 15/1484; G01N 2015/0065; G01N 2015/1006
See application file for complete search history.

(56) References Cited

U.S. PATENT DOCUMENTS

| 4,732,479 A | * | 3/1988 | Tanaka ................ G01N 15/1434 356/336 |
| 7,180,221 B1 | * | 2/2007 | Torres .................. H10N 30/202 310/329 |
| 2008/0260577 A1 | * | 10/2008 | Shirai .................... G01N 21/01 422/52 |
| 2012/0085894 A1 | | 4/2012 | Zhong et al. |
| 2015/0293021 A1 | * | 10/2015 | Finkelstein ........... G01S 7/4865 506/13 |
| 2016/0160276 A1 | * | 6/2016 | Earney ............... G01N 21/6428 506/13 |
| 2017/0061619 A1 | * | 3/2017 | Lagae ................ G01N 15/1434 |
| 2018/0155781 A1 | | 6/2018 | McCaffrey et al. |

FOREIGN PATENT DOCUMENTS

| DE | 19748211 A1 | 5/1999 |
| JP | 2010175419 A | 8/2010 |

* cited by examiner

*Primary Examiner* — Christine T Mui
*Assistant Examiner* — Jonathan Bortoli
(74) *Attorney, Agent, or Firm* — Bridgeway IP Law Group, PLLC; Jihun Kim (57) ABSTRACT

Disclosed are an optical analysis device and an optical analysis method. The present invention provides an optical analysis device for optically analyzing a flow cell, including: a light source configured to emit light to the flow cell; an optical detector including a plurality of detection elements that detects optical signals from reaction regions of the flow cell; and an optical mask including light transmissive mask holes disposed at a front end of each of the detection elements, and an optical analysis method using the same.

16 Claims, 7 Drawing Sheets

OPTICAL ANALYSIS DEVICE AND OPTICAL ANALYSIS METHOD

CROSS-REFERENCE TO RELATED APPLICATIONS

This application claims priority to and the benefit of Korean Patent Application No. 10-2019-0140762 filed in the Korean Intellectual Property Office on Nov. 6, 2019, the entire contents of which are incorporated herein by reference.

TECHNICAL FIELD

The present invention relates to an optical analysis device and an optical analysis method, and more particularly, to an optical analysis device and an optical analysis method for biologically or chemically analyzing genes and the like.

BACKGROUND ART

With recent advances in scientific technology, personalized medical technology is developing that tests the expression level of a patient's gene or protein or mutation of a gene, and selects a treatment method for the patient based on the test.

Next Generation Sequencing (NGS) creates a new turning point in the gene analysis. The NGS is the method of quickly deciphering vast genome information by breaking down one genome into countless fragments, reading the nucleotide sequence of each fragment at the same time, and then combining the DNA fragments by using computer technology.

An example of NGS is as follows. First, a DNA is cut into fragments, and then adaptors are attached to both ends of the DNA fragments to prepare a library. The prepared DNA library flows into wells of a flow cell to which complementary oligos to the adaptors are attached, and the adaptors are bound to the oligos and are amplified. In this process, the adaptors on the DNA fragments are attached to the surface of the flow cell to form bridges, and then DNA clusters composed of bridges are created, and one DNA cluster is composed of one type of bridge. Then, the base sequence is decoded by using the sequencing by synthesis that measures fluorescence that appears when a base is intervened during DNA synthesis. The base sequence deciphering is performed in the unit of a cluster. When a reaction in which the complementary base binds to the base of the DNA fragment occurs, fluorescent light of the base is emitted. Different colors of fluorescent lights may be emitted for each base A, G, C, and T, and the base sequence is decoded by analyzing the image according to each reaction to determine the sequence of the bases.

However, since a plurality of clusters is formed in the flow cell and an image sensor also exists as a plurality of pixels, there is a problem in that fluorescent signals of the surrounding clusters flow into the image sensor and becomes noise.

In the meantime, US Patent Application Publication No. 2012/0085894 discloses an integrated device provided with a nano hole and a channel optical waveguide. However, the device can detect one type of the clusters which is composed of one type of the bridges per pixel of an image sensor at a time, so that in the case of two or more kinds of clusters on the flow cell having a pattern that is more integrated than the pixel size of the image sensor (for example, an interval between the clusters is smaller than the interval between the image pixels), there is a problem in that effective detection is difficult.

In the case of the NGS equipment in the related art, there is a problem in that a complex optical system is required, or a large amount of reagent is consumed due to the size of the flow cell. Further, the improvement of a sequencing speed is an issue that needs to be continuously improved in the NGS.

SUMMARY OF THE INVENTION

The present invention has been made in an effort to provide an optical analysis device and an optical analysis method which is capable of decreasing noise and improving a measurement range.

The present invention has also been made in an effort to provide an optical analysis device and an optical analysis method which is capable of detecting integrated clusters and improves a sequencing speed without a complex optical system.

An exemplary embodiment of the present invention provides an optical analysis device for optically analyzing a flow cell, including: a light source configured to emit light to the flow cell; an optical detector including a plurality of the detection elements that detect optical signals from the reaction regions of the flow cell; and an optical mask including light transmissive mask holes disposed at a front end of each of the detection elements.

In the exemplary embodiment, the optical analysis device further includes a head unit in which the optical detector and the optical mask are installed, and which is configured to be moved by a driving unit.

The optical analysis device may further include a stage on which the flow cell is loaded.

In the exemplary embodiment, an assembly of the optical detector and the optical mask and the light source may be disposed at opposite sides based on the flow cell, thereby simplifying the configuration of the optical analysis device.

In the exemplary embodiment, the head unit is provided with a minute driving unit which minutely drives the assembly of the optical detector and the optical mask.

In the exemplary embodiment, a size of the mask hole is smaller than a size of the detection element.

The size of the mask hole may be smaller than a size of a well that is the reaction region of the flow cell.

A pixel size of the detection element may be the same or appropriately same as an interval between the wells.

In the exemplary embodiment, a specific detection element of the optical detector and a mask hole corresponding to the specific detection element may be used for recognizing an align mark formed in the flow cell.

In the exemplary embodiment, the reaction regions of the flow cell existing in a region photographable one time by the optical detector one to one correspond to a combination of the detection elements and the mask holes.

In the exemplary embodiment, the reaction regions of the flow cell existing in a region photographable one time by the optical detector may be more than the combinations of the detection elements and the mask holes.

The reaction regions of the flow cell may be at least divided into a first cluster group and a second cluster group adjacent to the first cluster group, and the assembly of the optical detector and the optical mask may be minutely shifted relative with respect to the flow cell after detecting fluorescent signals for the first cluster group and detect optical signals for the second cluster group.

The first cluster group and the second cluster group may be repeatedly disposed.

A pixel size of the detection elements may be formed to be larger than an interval between the wells that are the reaction regions.

Another exemplary embodiment of the present invention provides an optical analysis method including: (a) preparing an optical analysis device including a head unit including an optical detector including a plurality of the detection elements and an optical mask which is disposed at a front end of each of the detection elements and is formed with light transmissive mask holes, and a light source emitting light; (b) loading a flow cell to the optical analysis device; and (c) performing optical analysis for a reaction regions of the flow cell while relatively moving the head unit with respect to the flow cell.

In the exemplary embodiment, the method may further include after operation (b), aligning an assembly of the optical detector and the optical mask of the head unit with the flow cell by using an align mark formed in the flow cell.

The aligning may be performed by recognizing the align mark through a specific detection element of the optical detector and a mask hole corresponding to the specific detection element.

In the exemplary embodiment, the reaction regions of the flow cell existing in a region photographable one time by the optical detector may be more than the combinations of the detection elements and the mask holes.

The reaction regions of the flow cell may be at least divided into a first cluster group and a second cluster group adjacent to the first cluster group, and operation (c) may include: (c1) performing an optical analysis on the first cluster group; (c2) moving the head unit relative to the flow well to the location of the second cluster group; and (c3) performing the optical analysis on the second cluster group.

The first cluster group and the second cluster group may be repeatedly disposed.

According to the present invention, the optical mask is provided, so that fluorescent signals from the surrounding wells are prevented when the detection element obtains the fluorescent signal from a specific well, thereby decreasing noise.

According to the present invention, it is possible to effectively perform an optical analysis on DNA clusters on an integrated patterned flow cell through a relative minute shift of the optical detector (and the optical mask) for the flow cell.

According to the present invention, it is possible to relatively rapidly detect fluorescent signals for a flow cell compared to scanning a flow cell having a large area using an area camera or a scan camera.

According to the present invention, it is possible to simplify a configuration of a fluorescent analysis device, and utilize a flow cell having wells which are disposed in integrated pattern, thereby achieving an additional advantage of reducing the use of a reagent.

The foregoing summary is illustrative only and is not intended to be in any way limiting. In addition to the illustrative aspects, embodiments, and features described above, further aspects, embodiments, and features will become apparent by reference to the drawings and the following detailed description.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, exemplary embodiments of the present invention will be described in detail with reference to the accompanying drawings. First of all, it should be noted that in giving reference numerals to elements of each drawing, like reference numerals refer to like elements even though like elements are shown in different drawings. Further, in the following description of the present invention, a detailed description of known configurations or functions incorporated herein will be omitted when it is judged that the detailed description may make the subject matter of the present disclosure unclear. It should be understood that although the exemplary embodiment of the present invention is described hereafter, the spirit of the present invention is not limited thereto and the present invention may be changed and modified in various ways by those skilled in the art.

An optical analysis device and an optical analysis method according to the present invention are for a biological or chemical optical analysis and may be utilized in, for example, sequencing DNA (deoxyribonucleic acid). Hereinafter, the present invention will be described based on DNA sequencing, but the technical spirit of the present invention is not limited to the DNA sequencing.

Figure 1:
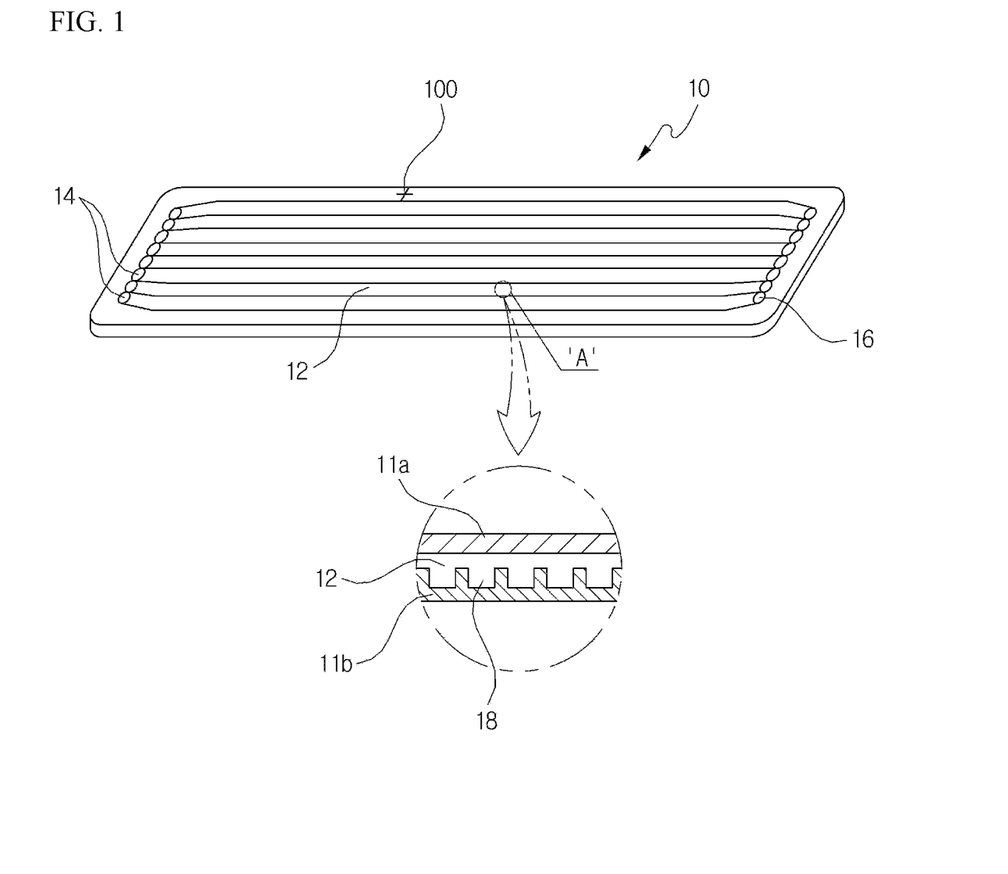
FIG. 1 is a diagram illustrating an example of a flow cell.

FIG. 1 is a diagram illustrating an example of a flow cell, and an enlarged cross-section of portion A of FIG. 1 is also illustrated.

A flow cell 10 is provided with at least one fluid channel 12, and a plurality of wells 18 functioning as the reaction regions are formed in the fluid channel 12. The DNA fragments may be attached to the plurality of wells 18 while forming clusters. The plurality of wells 18 may be formed in various patterns, such as a grid form or a zigzag form. The fluid channel 12 is connected with an inlet 14 for supplying a reagent containing a base that complementarily binds to the DNA clusters and an outlet 16 for discharging the reagent.

The flow cell 10 may be formed of a base panel 11b forming a lower structure and a cover 11a covering an upper portion of the fluid channel 12. Further, the base panel 11b and the fluid channel 12 may be formed of a light transmitting material. For the DNA sequencing, the well 18 of the flow cell 10 may be prepared in the state where the DNA clusters are attached to the well 18.

Figure 2:
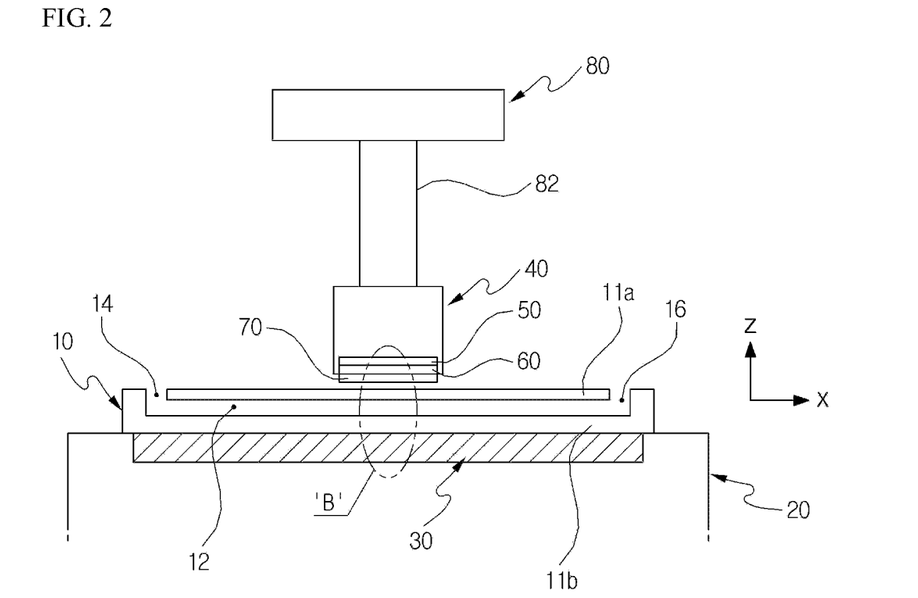
FIG. 2 is a diagram schematically illustrating an optical analysis device according to an exemplary embodiment of the present invention.
Figure 3:
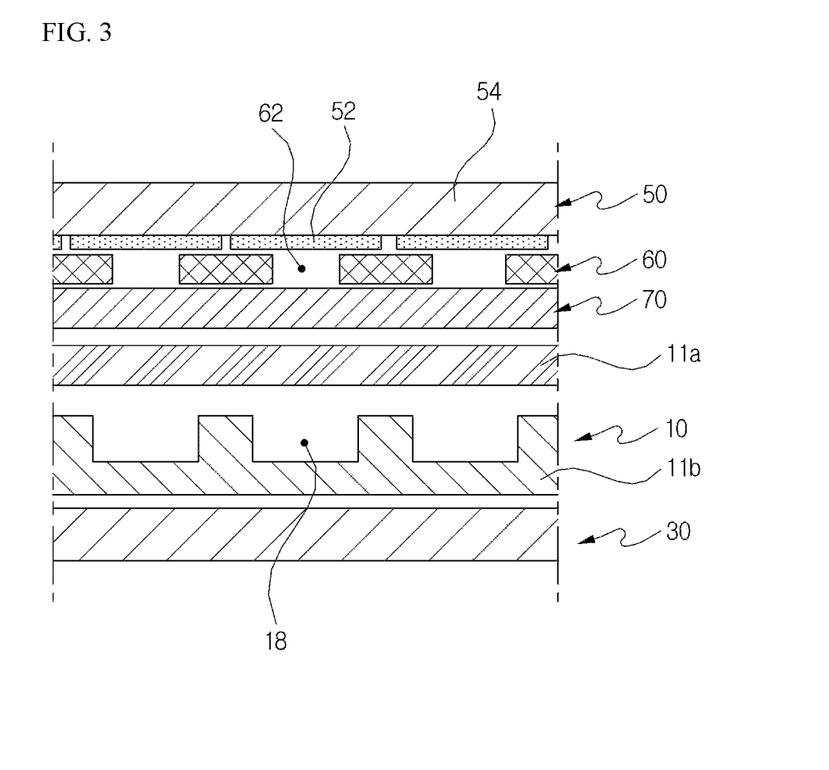
FIG. 3 is a diagram (an enlarged cross-sectional view of portion B of FIG. 2) illustrating a detailed configuration of the optical analysis device according to the exemplary embodiment of the present invention.

FIG. 2 is a diagram schematically illustrating an optical analysis device according to an exemplary embodiment of the present invention, and FIG. 3 is a diagram (an enlarged cross-sectional view of portion B of FIG. 2) illustrating a detailed configuration of the optical analysis device according to the exemplary embodiment of the present invention.

Referring to FIGS. 2 and 3, the optical analysis device according to the exemplary embodiment of the present invention includes a stage 20 on which the flow cell 10 is loaded, a light source 30 which emits light for the fluorescent analysis of the DNA clusters attached to the flow cell 10, and a head unit 40 for obtaining the fluorescent signals. Further, the optical analysis device according to the exemplary embodiment of the present invention may additionally include a driving unit 80 for driving the head unit 40.

The head unit 40 may include an optical detector 50 which converts the fluorescent signals into electric signals, and an optical mask 60 for decreasing noise when the fluorescent signals are obtained. Further, the head unit 40 may additionally include an optical filter 70 which filters light of a specific wavelength band when the fluorescent signals are detected.

The stage 20 performs a function of loading and supporting the flow cell 10. The stage 20 may be provided in a fixed form, and may also be provided to be driven in at least one direction on a plane depending on a case. In FIG. 2, a horizontal direction is indicated with an X-axis, a vertical direction is indicated with a Z-axis, and a direction vertical to the ground is a Y-axis. When the stage 20 is provided to be driven, the stage 20 may be driven in at least one direction between the X-axis and the Y-axis to adjust a relative location of the flow cell 10 and the head unit 40. Further, the stage 20 may be driven in the Z-axis to adjust an interval between the flow cell 10 and the head unit 40.

The light source 30 may be provided under the flow cell 10. In the exemplary embodiment, the light source 30 is located in an opposite side of the optical detector 50 based on the flow cell 10. The light source 30 may be disposed in the lateral portion of the optical detector 50 or coaxially disposed with the optical detector 50, but when the light source 30 is disposed as illustrated in FIG. 2, there is an advantage in that it is possible to simplify a disposition structure of the light source 30. In the exemplary embodiment, the light source 30 may be provided as a surface light source. Further, in the exemplary embodiment, the light source 30 may be provided in the form of an optical waveguide, and light generated from a separate light generator may be transmitted through the optical waveguide and light may be emitted to the flow cell 10.

The optical detector 50 may be formed of a substrate 54 and a plurality of detection elements 52 formed in the substrate 54. The detection element 52 detects a fluorescent signal, and converts the fluorescent signal into an electric signal. The detection element 52 may be implemented by a CCD or CMOS method to form one pixel. Further, the light detector 50 may be implemented in an image sensor in which the plurality of detection elements (that is, pixels) is arranged in an array form. When the optical detector 50 is implemented with the image sensor in which the plurality of pixels is arranged in the array form, a fluorescent signal is detected by each pixel and a detection result of the fluorescent signal may be obtained as one or more images.

The optical mask 60 includes mask holes 62 formed to penetrate while corresponding to the detection elements 52 or formed to allow light to pass, and a portion except for the mask holes 62 is formed of a material through which light does not pass. The optical mask 60 may be formed of a flat plate shape in which the plurality of mask holes 62 is formed. In the exemplary embodiment, the mask hole 62 of the optical mask 60 may be formed to be smaller than the pixel size of the detection element 52. A fluorescent signal in a specific well 18 may be incident based on a center of the detection element 52 by the mask hole 62. The mask hole 62 may be formed in a quadrangular shape, but may also be provided in a shape of a circle, a triangle, and the like, not a quadrangle. The optical mask 60 allows the fluorescent signal in the specific well 18 to be transmitted to the corresponding detection element 52 and prevents the fluorescent signals from the surrounding wells 18 from being incident. In the exemplary embodiment, the size of the mask hole 62 may be formed to be smaller than the size of the well 18.

In the exemplary embodiment, the optical detector 50 and the optical mask 60 may be fixed to the head unit 40 in the state where the detection elements 52 and the mask holes 62 are disposed to match.

The driving unit 80 is an element for driving the head unit 40 in at least one direction, and may be formed by a driving means, such as a linear motor. The driving unit 80 may be connected with the head unit 40 through the head unit supporting unit 82. The driving unit 80 may move the head unit 40 in at least one direction between the X-axis and the Y-axis of FIG. 2. Further, the driving unit 80 may be additionally provided with a driver that drives the head unit 40 in the Z-axis direction.

Figure 4:
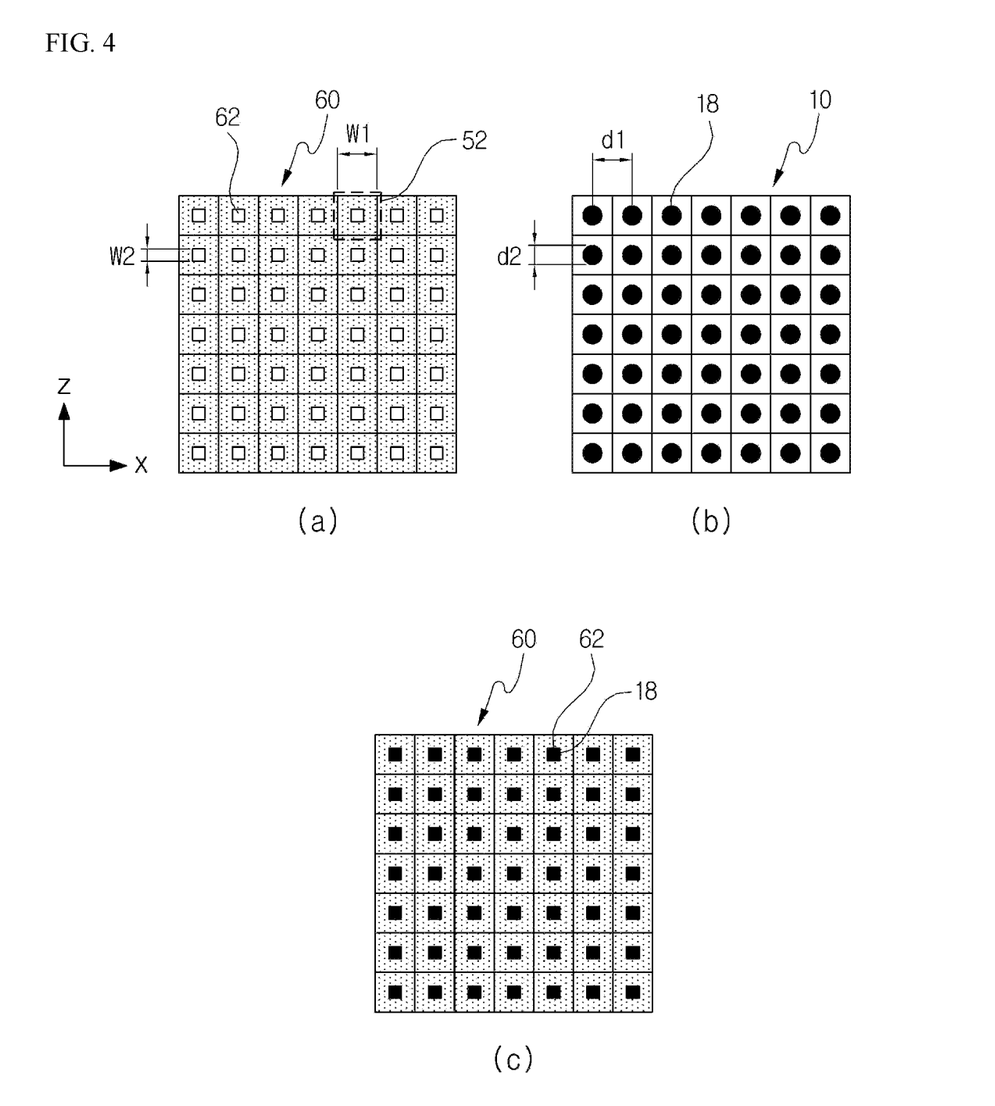
FIG. 4 is a diagram describing a location relation between an optical mask and a well (clusters) of a flow cell in the optical analysis device according to the exemplary embodiment of the present invention.

FIG. 4 is a diagram describing a location relation between the optical mask and the well (cluster or clusters) of the flow cell in the optical analysis device according to the exemplary embodiment of the present invention.

(a) of FIG. 4 illustrates the optical mask 60 in which the mask holes 62 are formed. In each mask hole 62 of the optical mask 60, the detection element 52 corresponding to the mask hole 62 is located. In (a) of FIG. 4, a pixel size of the detection element 52 is w1 and a size of the mask hole 62 is w2 (w2 may be a diameter where the mask hole 62 has a circular shape). w2 is smaller than w1, so the fluorescent signal from the periphery of the specific well 18 may be prevented from spreading to the surrounding detection elements 52 by the mask hole 62. The center of the mask hole 62 may be disposed to be matched with the center of the detection element 52.

(b) of FIG. 4 illustrates the disposition of the plurality of wells 18 formed in the flow cell 10. An interval between the adjacent wells 18 is d1 and a size (or a diameter) of the well 18 is d2. The interval d1 between the wells 18 may be defined with a distance between the centers of the adjacent wells 18. In the exemplary embodiment of the present invention, the pixel size w1 may be the same or approximately the same as the interval d1 between the wells 18. The size w2 of the mask hole 62 may be smaller than the size d2 of the well 18. In the case where the size w2 of the mask hole 62 is formed to be smaller than the size d2 of the well 18, it is possible to further prevent an inflow of noise other than the fluorescent signal from the specific well 18.

(c) of FIG. 4 illustrates a state where the optical mask 60 is disposed in upper portions of the wells 18 of the flow cell 10.

(a) to (c) of FIG. 4 illustrate the example in which the mask holes 62 are formed in the form of 7×7 but the number of mask holes 62 may be increased according to an actual size of the optical mask 60.

After a detection of fluorescent signals is completed for a partial region of the flow cell 10 corresponding to a photographing possible region of the optical detector 50, at least one of the head unit 40 and the stage 20 is driven, so that the head unit 40 is located in the not-photographed region of the flow cell 10 and the detection of the fluorescent signals for the regions is performed.

In the meantime, referring to FIG. 1, an align mark 100 may be formed in the flow cell 10. The align mark 100 may serve as a reference for aligning the head unit 40 in the flow cell 10. The align mark 100 illustrated in FIG. 1 is merely an example, and it is also possible to change the location of the align mark 100 or increase the number of align marks 100 as necessary.

In the exemplary embodiment, the align mark 100 may be provided based on the center of the specific hole 18 provided in the flow cell 10. The specific mask hole 62 among the plurality of mask holes 62 of the optical mask 60 and the detection element 52 corresponding to the specific mask hole 62 may be used for alignment using the align mask 100. When the align mark 100 is located at the center of the specific detection element 52, it may be determined that the detection element 52, the mask hole 62, and the well 18 are accurately aligned. When the align mark 100 is not accurately recognized, the detection element 52, the mask hole 62, and the well 18 may be aligned by finely shifting the head unit 40 or the stage 20.

Figure 5:
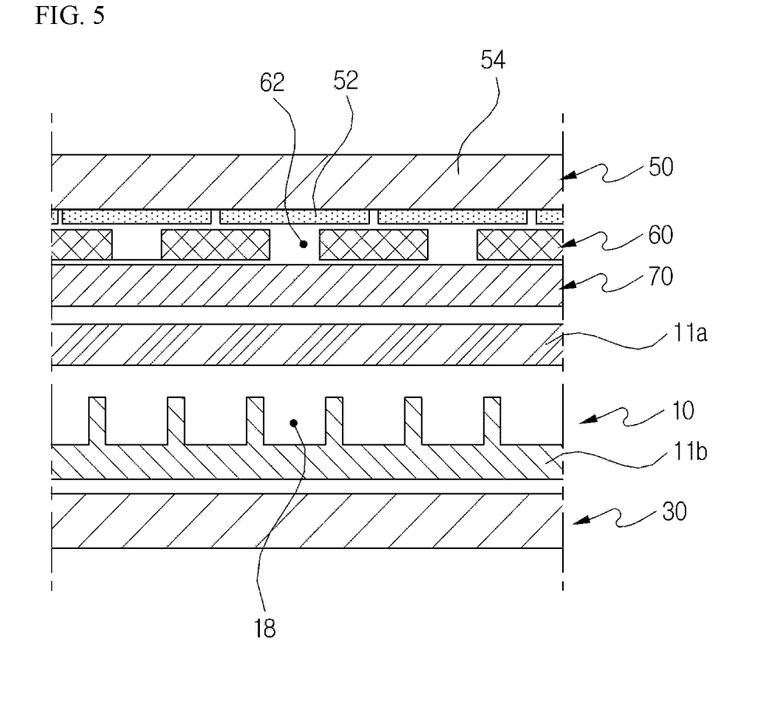
FIG. 5 is a diagram illustrating a detailed configuration of an optical analysis device according to another exemplary embodiment of the present invention.
Figure 6:
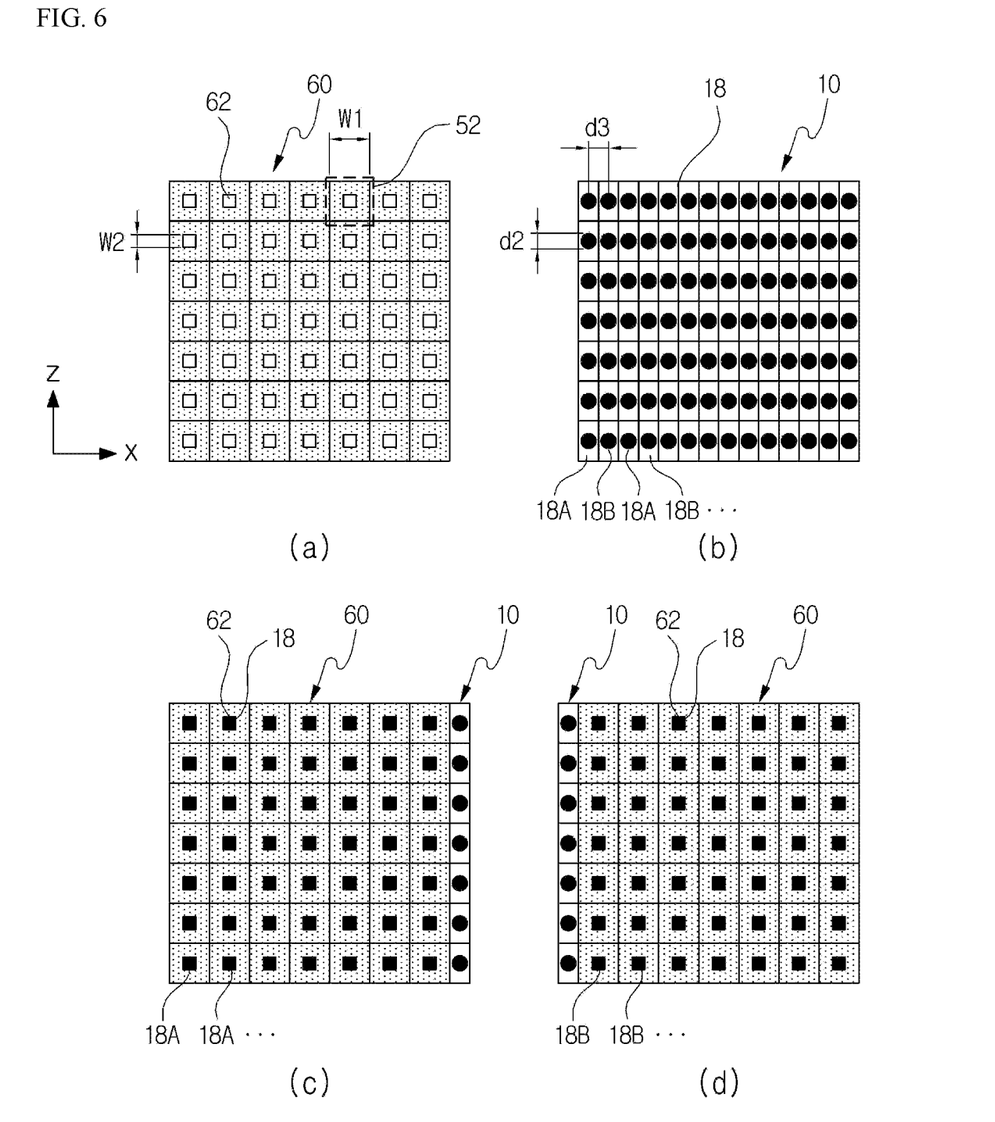
FIG. 6 is a diagram describing a location relation between an optical mask and a well (clusters) of a flow cell in the optical analysis device according to another exemplary embodiment of the present invention.

FIG. 5 is a diagram illustrating a detailed configuration of an optical analysis device according to another exemplary embodiment of the present invention, and FIG. 6 is a diagram describing a location relation between an optical mask and a well (cluster or clusters) of a flow cell in the optical analysis device according to another exemplary embodiment of the present invention.

Referring to FIGS. 5 and 6, the optical analysis device is different from the configuration of FIGS. 3 and 4 in that the number of wells 18 is larger than the number of detection elements 52 or mask holes 62. In FIGS. 5 and 6, it is exemplified that the number of wells 18 in a region covered by an optical detector 50 is two times the number of detection elements 52 or the mask holes 62. However, in the exemplary embodiment of the present invention, the number of wells 18 is three or four times the number of detection elements 52 or the mask holes 62. Further, in FIG. 6, it is exemplified that the number of wells 18 in the X-axis direction is two times more, but it is possible to double the number of wells 18 not only in the X-axis direction but also in the Y-axis direction as a matter of course.

(a) of FIG. 6 illustrates the optical mask 60 in which the mask holes 62 are formed, and (b) of FIG. 6 illustrates the disposition of the plurality of wells 18 formed in the flow cell 10 in which the wells 18 are disposed in 14 columns in the X-axis direction.

Referring to (b) of FIG. 6, from the left column, first cluster groups 18A and second cluster groups 18B are alternately disposed. In this case, a distance between the first cluster group 18A and the second cluster group 17B is d3, and d3=(w1)/2.

(c) of FIG. 6 illustrates a detection of fluorescent signals for the first cluster group 18A and (d) of FIG. 6 illustrates a detection of fluorescent signals for the second cluster group 18B.

Referring to (c) of FIG. 6, a head unit 40 is relatively located to the flow cell 10 so that the fluorescent signals of the first cluster group 18A pass through the mask holes 62. In the state of (c) of FIG. 6, the optical detector 50 detects the fluorescent signals for the first cluster group 18A.

Referring to (d) of FIG. 6, the head unit 40 is relatively located to the flow cell 10 so that the fluorescent signals of the second cluster group 18B pass through the mask holes 62 by driving the head unit 40 in a positive direction of the X-axis, driving a stage 20 in a negative direction of the X-axis, or driving both the head unit 40 and the stage 20. In the state of (d) of FIG. 6, the optical detector 50 detects the fluorescent signals for the second cluster group 18B.

The inflow of the signals from the adjacent wells 18 in addition to the fluorescent signal from the corresponding well 18 to the corresponding detection element 52 are prevented or minimized by the mask holes 62 of the optical mask 60. Further, according to the exemplary embodiments of FIGS. 5 and 6, the efficient and rapid detection of the fluorescent signals may also be performed on the clusters having the more integrated pattern than the detection element 52.

Figure 7:
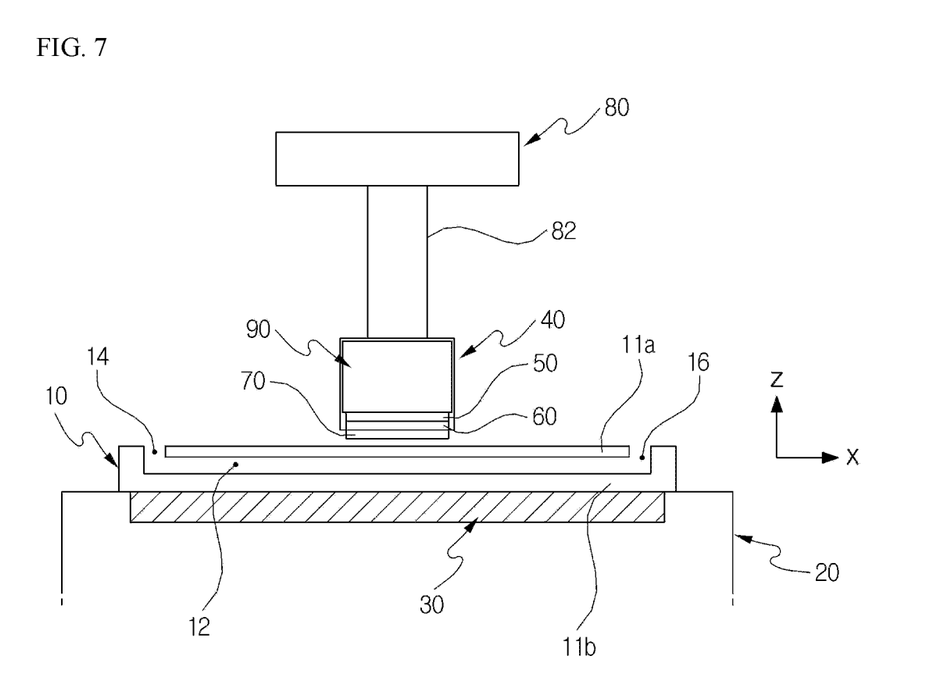
FIG. 7 is a diagram schematically illustrating an optical analysis device according to still another exemplary embodiment of the present invention.

FIG. 7 is a diagram schematically illustrating an optical analysis device according to still another exemplary embodiment of the present invention.

The exemplary embodiment illustrated in FIG. 7 is different from the exemplary embodiment illustrated in FIG. 2 in that a minute driving unit 90 for minutely shifting an optical detector 50 and an optical mask 60 is additionally provided in a head unit 40.

The minute driving unit 90 may minutely shift a coupled body of the optical detector 50 and the optical mask 60. In the exemplary embodiment, the minute driving unit 90 includes a minute driving stage driven by a piezo scheme, and may be formed so that the optical detector 50 and the optical mask 60 are installed on the driving stage. In the case where the minute driving unit 90 is additionally provided, a large movement of the head unit 40 is performed by a driving unit 80, and a movement from (c) of FIG. 6 to (d) of FIG. 6 may be performed by the minute driving unit 90.

Next, an optical analysis method according to an exemplary embodiment of the present invention will be described.

Figure 8:
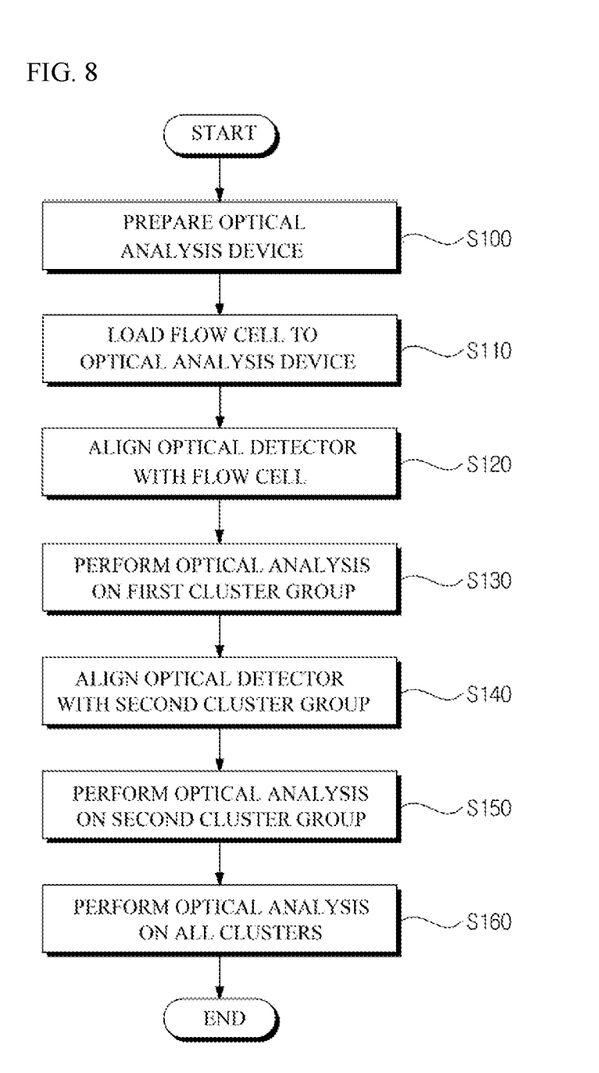
FIG. 8 is a flowchart illustrating an optical analysis method according to an exemplary embodiment of the present invention.

FIG. 8 is a flowchart illustrating an optical analysis method according to an exemplary embodiment of the present invention.

First, the optical analysis device is prepared (S100). The head unit 40 is prepared in the state where the optical detector 50 and the optical mask 60 are coupled, and the light source 30 for obtaining fluorescent signals is prepared. The optical analysis device may include the stage 20 for loading the flow cell 10, and the light source 30 may be disposed so as to be disposed under the flow cell 10.

After the optical analysis device is prepared, the flow cell 10 to which the DNA clusters are attached is loaded to the optical analysis device (S110).

The optical detector 50 is aligned with the flow cell 10 (S120). That is, S120 is the process of aligning an assembly of the optical detector 50 and the optical mask 60 in the flow cell 10. The alignment of the optical detector 50 may be performed by recognizing the align mark formed in the flow cell 10. In this case, the head unit 40 may be moved by using the driving unit 80, the minute driving unit 90 which is provided in the head unit 40 and minutely shifts the assembly of the optical detector 50 and the optical mask 60 may be driven, or the stage 20 on which the flow cell 10 is loaded may be moved. In the exemplary embodiment, the alignment in operation S120 may be performed by making the align mark be located in the specific detection element 52 of the optical detector 50 and the specific mask hole 62 of the optical mask 60 corresponding to the specific detection element 52. To this end, the detection element 52 located at the specific location among the plurality of detection elements may be set as the detection element for recognizing the align mark. When the align mark is recognized in another detection element, not the specific detection element 52, the head unit 40, the stage 20, or the minute driving unit 90 may be driven so that the align mark is recognized in the specific detection element 52.

After the alignment of operation S120 is completed, an optical analysis is performed by sequentially detecting the fluorescent signals for the entire region of the flow cell 10. This process may be performed by obtaining the fluorescent signals while relatively moving the head unit 40 with respect to the flow cell 10.

An additional operation of the optical analysis method for the case where the flow cell 10, the optical detector 50, and the optical mask 60 are provided like FIGS. 5 and 6 will be described as follows.

After the alignment according to operation S120 is completed, an optical analysis is performed on the first cluster group 18A (S130). In the state where the detection element 52 of the optical detector 50 and the mask hole 62 corresponding to the detection element 52 are aligned with the wells 18 belonging to the first cluster group 18A, the fluorescent signals from the first cluster group 18A are detected by the detection elements 52, respectively. The light source 30 may be turned on in operation S130 to initiate an emission of light. The fluorescent signals of the wells 18 belonging to the first cluster group 18A are transmitted to the detection elements 52 through the mask holes 62 of the optical mask 60, respectively.

After operation S130 is completed, the assembly of the optical detector 50 and the optical mask 60 is aligned with the second cluster group 18B (S140). At least one of the head unit 40 or the stage 20 or the minute driving unit 90 is driven so that the detection elements 52 of the optical detector 50 and the mask holes 62 corresponding to the detection elements 52 are aligned with the wells 18 belonging to the second cluster group 18B. In the exemplary embodiment, after operation S130 is completed, the light source 30 is turned off, and the light source 30 may be turned on again at the time when operation S150 is performed.

After operation S140, the optical analysis is performed on the second cluster group 18B (S150). The fluorescent signals of the wells 18 belonging to the second cluster group 18B are transmitted to the detection elements 52 through the mask holes 62 of the optical mask 60, respectively.

The optical analysis is performed on all of the clusters by repeatedly performing the optical analysis on other clusters from which the fluorescent signals are not obtained (S160).

Although the exemplary embodiment of the present invention has been described for illustrative purposes, those skilled in the art will appreciate that various modifications, additions and substitutions are possible, without departing from the scope and spirit of the invention. Therefore, the embodiments disclosed in the present invention and the accompanying drawings are not intended to limit the technical spirit of the present invention, but are intended to illustrate the scope of the technical idea of the present invention, and the scope of the present invention is not limited by the embodiment and the accompanying drawings. The scope of the present invention shall be construed on the basis of the accompanying claims in such a manner that all of the technical ideas included within the scope equivalent to the claims belong to the scope of the present invention.

Meanwhile, the embodiments according to the present invention may be implemented in the form of program instructions that can be executed by computers, and may be recorded in computer readable media. The computer readable media may include program instructions, a data file, a data structure, or a combination thereof. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An optical analysis device for optically analyzing a flow cell, the optical analysis device comprising:
    a light source configured to emit light to the flow cell;
    an optical detector including a substrate and a plurality of detection elements arranged on the substrate in an array form, the plurality of detection elements being configured to detect optical signals from a plurality of reaction regions of the flow cell; and
    an optical mask including a plurality of mask holes that are light transmissive, each of the plurality of mask holes being disposed at a front end of each of the plurality of detection elements,
    wherein the number of the plurality of reaction regions is greater than the number of the plurality of mask holes,
    wherein the plurality of reaction regions in the flow cell form at least a set of a first cluster group of reaction regions and a second cluster group of reaction regions, the second cluster group being adjacent to the first cluster group, and
    wherein the optical analysis device further comprises a piezo driving unit that is configured to shift an assembly of the optical detector and the optical mask with respect to the flow cell after detecting fluorescent signals for the first cluster group to detect fluorescent signals for the second cluster group.

2. The optical analysis device of claim 1, further comprising:
    a head unit in which the optical detector and the optical mask are disposed, wherein the head unit is configured to be moved by a driving unit.

3. The optical analysis device of claim 1, further comprising:
    a stage on which the flow cell is loaded.

4. The optical analysis device of claim 1, wherein the assembly of the optical detector and the optical mask is disposed to be opposite to the light source such that the flow cell is disposed between the assembly and the light source.

5. The optical analysis device of claim 2, wherein the head unit includes the piezo driving unit.

6. The optical analysis device of claim 1, wherein a size of the respective mask hole is smaller than a size of the respective detection element.

7. The optical analysis device of claim 6, wherein the plurality of reaction regions include a plurality of wells, and the size of the respective mask hole is smaller than a size of the respective well.

8. The optical analysis device of claim 1, wherein a specific detection element of the optical detector and a mask hole corresponding to the specific detection element are used for recognizing an align mark formed in the flow cell.

9. The optical analysis device of claim 7, wherein a pixel size of the respective detection element is the same as an interval between two adjacent wells of the plurality of wells.

10. The optical analysis device of claim 1, wherein a reaction region of the flow cell existing in a region photographable one time by the optical detector corresponds to a combination of a detection element and a mask hole.

11. The optical analysis device of claim 1, wherein the plurality of reaction regions include a plurality of first cluster groups and a plurality of second cluster groups, in which the respective first cluster group is disposed next to the respective second cluster group.

12. The optical analysis device of claim 7, wherein a pixel size of the respective detection element is larger than an interval between two adjacent wells.

13. A method for optically analyzing a flow cell, the method comprising:
    (a) preparing an optical analysis device including: a light source configured to emit light to the flow cell; an optical detector including a substrate and a plurality of detection elements arranged on the substrate in an array form, the plurality of detection elements being configured to detect optical signals from a plurality of reaction regions of the flow cell; an optical mask including a plurality of mask holes that are light transmissive, each of the plurality of mask holes being disposed at a front end of each of the plurality of detection elements; and a piezo driving unit configured to shift an assembly of the optical detector and the optical mask with respect to the flow cell;
    (b) loading the flow cell onto the optical analysis device; and
    (c) performing optical analysis for the reaction regions of the flow cell while moving the assembly of the optical detector and the optical mask with respect to the flow cell,
    wherein the number of the plurality of reaction regions is greater than the number of the plurality of mask holes,
    wherein the plurality of reaction regions in the flow cell form at least a set of a first cluster group of reaction regions and a second cluster group of reaction regions, the second cluster group being adjacent to the first cluster group, and
    wherein (c) performing the optical analysis includes:
        (c1) performing the optical analysis on the first cluster group by detecting fluorescent signals for the first cluster group;
        (c2) shifting, by the piezo driving unit, the assembly of the optical detector and the optical mask with respect to the flow cell to a location of the second cluster group; and
        (c3) performing the optical analysis on the second cluster group by detecting fluorescent signals for the second cluster group.

14. The method of claim 13, further comprising:
    after (b) loading the flow cell, aligning the assembly of the optical detector and the optical mask with respect to the flow cell by using an align mark formed in the flow cell.

15. The method of claim 14, wherein the aligning is performed by recognizing the align mark through a specific detection element of the optical detector and a mask hole corresponding to the specific detection element.

16. The method of claim 13, wherein the plurality of reaction regions include a plurality of first cluster groups and a plurality of second cluster groups, in which the respective first cluster group is disposed next to the respective second cluster group.

* * * * *